US006602950B1

(12) United States Patent
Dentler et al.

(10) Patent No.: US 6,602,950 B1
(45) Date of Patent: Aug. 5, 2003

(54) HYDROPHILIC HYDROGELS WITH A HIGH SWELLING CAPACITY AND METHOD FOR PRODUCING AND USING THEM

(75) Inventors: Joachim Dentler, Bruchköbel (DE); Rüdiger Funk, Niedernhausen (DE); Norbert Herfert, Altenstadt (DE); Mariola Wanior, Erlensee (DE); Friedrich Engelhardt, Chesapeake, VA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/806,944

(22) PCT Filed: Oct. 1, 1999

(86) PCT No.: PCT/EP99/07308

§ 371 (c)(1),
(2), (4) Date: Apr. 6, 2001

(87) PCT Pub. No.: WO00/22018

PCT Pub. Date: Apr. 20, 2000

(30) Foreign Application Priority Data

Oct. 8, 1998 (DE) .......................................... 198 46 412

(51) Int. Cl.$^7$ .......................... A61L 15/24; A61L 15/60; C08F 220/06; C08F 251/00; C08L 33/08

(52) U.S. Cl. .................. 524/832; 252/194; 264/177.17; 516/105; 524/833; 524/916; 525/54.23; 525/54.26; 526/932; 604/368; 604/372; 604/904

(58) Field of Search ................................ 516/108, 105; 524/832, 835, 916; 264/177.17; 252/194; 604/368, 372, 904; 525/54.23, 54.26; 526/932

(56) References Cited

U.S. PATENT DOCUMENTS

| | | | |
|---|---|---|---|
| 4,076,663 A | | 2/1978 | Masuda et al. |
| 4,105,033 A | * | 8/1978 | Chatterjee et al. |
| 4,113,688 A | * | 9/1978 | Pearson .................. 524/916 X |
| 4,190,562 A | | 2/1980 | Westerman |
| 4,654,039 A | * | 3/1987 | Brandt et al. ............... 604/368 |
| 4,873,299 A | | 10/1989 | Nowakowsky et al. ....... 526/73 |
| 4,985,514 A | | 1/1991 | Kimura et al. ................ 526/88 |
| 5,275,773 A | * | 1/1994 | Irie et al. ................. 524/916 X |
| 5,453,323 A | | 9/1995 | Chambers et al. ........... 428/402 |
| 5,508,381 A | * | 4/1996 | Jang et al. ............... 604/372 X |
| 5,629,377 A | * | 5/1997 | Burgert et al. .............. 524/832 |
| 5,668,236 A | * | 9/1997 | Engelhardt et al. ...... 524/916 X |
| 5,747,570 A | | 5/1998 | Date et al. .................. 524/161 |

FOREIGN PATENT DOCUMENTS

| | | |
|---|---|---|
| DE | 26 12 846 | 10/1976 |
| DE | 195 29 348 | 2/1997 |
| EP | 0 205 674 | 12/1986 |
| EP | 0 303 440 | 2/1989 |
| EP | 0 238 050 | 10/1989 |
| EP | 0 530 438 | 3/1993 |
| EP | 0 629 411 | 12/1994 |
| EP | 0 640 330 | 3/1995 |
| WO | WO 95/22358 | 8/1995 |
| WO | WO 95/26209 | 10/1995 |
| WO | WO 97/06190 | 2/1997 |
| WO | WO 97/12575 | 4/1997 |

\* cited by examiner

*Primary Examiner*—Richard D. Lovering
(74) *Attorney, Agent, or Firm*—Oblon, Spivak, McClelland, Maier & Neustadt, P.C.

(57) ABSTRACT

A hydrophilic, highly swellable hydrogel based on (co) polymerized monomers or based on graft (co)polymers and prepared by a) free-radically (co)polymerizing one-or more hydrophilic monomers or graft (co)polymerizing one or more hydrophilic monomers onto a grafting base, the average degree of neutralization of the acid-functional monomers being from 0 to 40 mol %, b) comminuting the acidic hydrogel, c) neutralizing the acidic hydrogel to an ultimate degree of neutralization of 50–85 mol % by adding a neutralizing agent, d) drying, grinding and sieving the hydrogel particles characterized by a centrifuge retention and a vertical absorption swell height, each having a specified minimum.value, coupled with an extractables content having a specified maximum value or a centrifuge retention and a vertical absorption swell height, each having a specified minimum value and an extractables content having a specified maximum value.

23 Claims, No Drawings

HYDROPHILIC HYDROGELS WITH A HIGH SWELLING CAPACITY AND METHOD FOR PRODUCING AND USING THEM

This is a 371 of PCT/EP99/07308 filed Oct. 1, 1999.

The present invention relates to hydrophilic, highly swellable hydrogels having high absorbency for water and aqeuous fluids, to a process for their preparation and to the use of these hydrogels.

Hydrophilic hydrogels obtainable by polymerization of unsaturated acids, for example acrylic acid, methacrylic acid, acrylamidopropanesulfonic acid, etc., in the presence of small amounts of multiply olefinically unsaturated compounds are already known as superabsorbent polymers. Also known are hydrophilic hydrogels obtainable by graft copolymerization of the olefinically unsaturated acids onto different matrices, for example polysaccharides, polyalkylene oxides and derivatives thereof.

The hydrogels mentioned are notable for high absorbency for water and aqueous solutions and are therefore widely used as absorbents in hygiene articles.

Such water-swellable hydrophilic polymers are generally prepared by free-radical polymerization in an aqueous solution which contains the monomers with or without a grafting base and crosslinker.

The water-swellable hydrophilic polymers produced for use in the hygiene and sanitary sector have a degree of neutralization in the range from 50 to 85 mol % based on the polymerized acid-functional monomer units, so that the hydrogels formed in use are pH neutral with regard to the skin.

The degree of neutralization is generally set prior to the polymerization, since this avoids the technically difficult neutralization of an acidic hydrogel of high viscosity. However, the polymerization of, for example, acrylic acid in the neutral pH range is slower, and leads to lower molecular weights, than the polymerization in the acidic range. This is explained by the electrostatic repellency between the most recently incorporated monomer unit and the next monomer unit to be incorporated, which repellency arises only minimally, if at all, in the case of a polymerization in the acidic pH range, since the monomer units are present in the uncharged, acidic form.

The trend toward ever thinner diaper constructions requires water-swellable hydrophilic polymers providing better and better performance characteristics with regard to absorption capacity, fluid acquisition and fluid transportation within the hygiene article, especially under a confining load.

EP-A-0 640 330, WO 95/22358, WO 95/26209 and WO 97/12575 describe a test for measuring the gel permeability of swollen hydrogel particles (Saline Flow Conductivity, SFC). This test determines the flow of a sodium chloride solution through a preswollen hydrogel particle layer under a pressure of 0.3 psi. Since, in this test method, the sodium chloride solution will flow through the swollen gel layer in the direction of the force of gravity, this method is less suitable for characterizing any capillary forces. In practice, however, it is relevant for the quality of hygiene articles that fluid can be transported under load even in a direction opposite to the force of gravity, i.e., capillary forces do play an important part.

It is an object of the present invention to provide hydrophilic, highly swellable hydrogels having improved absorption properties, especially improved capillarity under load, and a process for the production thereof.

We have found that this object is achieved by a hydrophilic, highly swellable hydrogel based on (co)polymerized monomers or based on graft (co)polymers obtainable by a) free-radically (co)polymerizing one or more hydrophilic monomers or graft (co)polymerizing one or more hydrophilic monomers onto a grafting base, the average degree of neutralization of the acid-functional monomers being from 0 to 40 mol %, b) comminuting the acidic hydrogel, c) neutralizing the acidic hydrogel to an ultimate degree of neutralization of 50–85 mol % by adding a neutralizing agent, d) drying, grinding and sieving the hydrogel particles characterized by a centrifuge retention of at least 29 g/g for a 0.9% aqueous NaCl solution and a vertical absorption (1 g) swell height of at least 3.5 cm coupled with an extractables content (16 h value) of less than 5% or a centrifuge retention of at least 23 g/g for a 0.9% aqueous NaCl solution and a vertical absorption (3 g) swell height of at least 5 cm an extractables content (16 h value) of less than 4%.

The hydrophilic, highly swellable hydrogels of the invention and also the process for their production will now be more particularly described.

Hydrophilic monomers useful for preparing the water-swellable hydrophilic polymers of the invention include for example acids capable of addition polymerization, such as acrylic acid, methacrylic acid, vinylsulfonic acid, vinylphosphonic acid, styrenesulfonic acid, maleic acid, maleic anhydride, fumaric acid, itaconic acid, 2-acrylamido-2-methylpropanesulfonic acid, 2-acrylamido-2-methylpropanephosphonic acid and their amides, hydroxyalkyl esters, amino- or ammonio-functional esters and amides. Water-soluble N-vinylamides or else diallyldimethylammonium chloride are also suitable.

Preferred hydrophilic monomers are compounds of the general formula (I)

where $R^1$ is hydrogen, methyl or ethyl, $R^2$ is —COOR$^4$, hydroxysulfonyl, phosphonyl, a ($C_1$–$C_4$)-alkanol-esterified phosphonyl group or a group of the general formula (II)

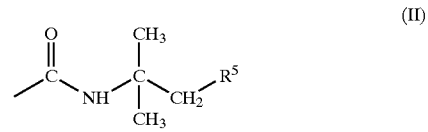

$R^3$ is hydrogen, methyl, ethyl or carboxyl, $R^4$ is hydrogen, amino-($C_1$–$C_4$)-alkyl or hydroxy-($C_1$–$C_4$)-alkyl, and $R^5$ is hydroxysulfonyl, phosphonyl or carboxyl.

Examples of ($C_1$–$C_4$)-alkanols are methanol, ethanol, n-propanol and n-butanol.

Particularly preferred hydrophilic monomers are acrylic acid and methacrylic acid.

When the monomers used are acids, their alkali metal or ammonium salts may be used as comonomers in a fraction of up to 40% by weight.

Useful grafting bases may be of natural or synthetic origin. Examples are starch, cellulose or cellulose derivatives and also other polysaccharides and oligosaccharides, polyvinyl alcohol, polyalkylene oxides, especially polyethylene oxides and polypropylene oxides, and also hydrophilic polyesters. Useful polyalkylene oxides have for example the formula (III)

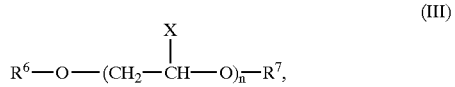

(III)

where
R$^6$ and R$^7$ are independently hydrogen, alkyl, alkenyl or aryl,
X is hydrogen or methyl, and
n is an integer from 1 to 10000.

R$^6$ and R$^7$ are each for example linear or branched (C$_1$–C$_{10}$)-alkyl such as methyl, ethyl, propyl, isopropyl, n-butyl, (C$_2$–C$_6$)-alkenyl or aryl such as unsubstituted or (C$_1$–C$_4$)-alkyl-substituted phenyl.

R$^6$ and R$^7$ are each preferably hydrogen, (C$_1$–C$_4$)-alkyl, (C$_2$–C$_6$)-alkenyl or phenyl.

The hydrophilic, highly swellable hydrogels are preferably in a crosslinked state, i.e., they contain units polymerized into the polymer network that are derived from compounds having at least two double bonds.

Useful crosslinkers include in particular methylenebisacrylamide, methylenebismethacrylamide, esters of unsaturated mono- or polycarboxylic acids with polyols, such as diacrylate or triacrylate, e.g., butanediol diacrylate, butanediol dimethacrylate, ethylene glycol diacrylate, ethylene glycol dimethacrylate and also trimethylolpropane triacrylate, allyl compounds such as allyl (meth)acrylate, triallyl cyanurate, diallyl maleate, polyallyl esters, tetraallyloxyethane, triallylamine, tetraallylethylenediamine, pentaerythritol triallyl esters or allyl esters of phosphoric acid and also vinyl compounds such as vinyl acrylate, divinyl adipate, divinylbenzene and vinylphosphonic acid derivatives, as described for example in EP-A-0 343 427.

The polymerization may be initiated using high energy electromagnetic radiation or the customary chemical polymerization initiators, for example organic peroxides such as benzoyl peroxide, tert-butyl hydroperoxide, methyl ethyl ketone peroxide, cumene hydroperoxide, azo compounds such as azodiisobutyronitrile and also inorganic peroxy compounds such as ammonium persulfate, potassium persulfate or hydrogen peroxide, with or without reducing agents such as sodium bisulfite, and iron(II) sulfate or redox systems where the reducing component is an aliphatic or aromatic sulfinic acid, such as benzenesulfinic acid or toluenesulfinic acid or derivatives thereof, for example Mannich adducts of sulfinic acid, aldehydes and amino compounds.

Polymerization in aqueous solution is preferably conducted as a gel polymerization by utilizing the Trommsdorff-Norrish effect. It is particularly preferable for the polymerization to be carried out in the quiescent state without mechanical mixing, so that the hydrogel that forms is not exposed to any mechanical shearing forces which would raise the level of extractables. The polymerization may here be carried out not only batchwise, for example in a cylindrical reactor, but also continuously, for example by polymerization on a belt reactor.

The resultant hydrogels are coarsely comminuted by means of customary pulling and/or cutting tools, for example by the action of a discharging pump in the case of a polymerization in a cylindrical reactor or by a cutting roll or cutting roll combination in the case of a belt polymerization.

This provides provides acidic hydrogel particles which have to be adjusted to the desired ultimate degree of neutralization of 50–85 mol % based on acid-functional monomer units by neutralizing these acid-functional monomer units. This neutralization is a process which is technically difficult to carry out and which has to meet particular requirements. First, the gel must not be excessively sheared during the contacting with the neutralizing agent so as to avoid increasing the extractables content, which would have an adverse effect on the properties of the end product and accordingly is undesirable, and, secondly, neutralization has to be completely homogeneous.

The subsequent neutralization of acidic hydrogels is known in principle.

DE-A-26 12 846 discloses a process for preparing a water-absorbing resin by polymerizing at least one starch and/or cellulose with at least one water-soluble monomer having a polymerizable double bond and with a crosslinker. The polymers obtained are neutralized with alkalis, although the method of neutralization is not more particularly specified.

According to EP-A-0 205 674, acidic polymers are prepared at from 0 to 100° C., preferably from 5 to 40° C., and their pH is adjusted by subsequent partial neutralization of the hydrogel. Neutralization is effected here by adding the gel to a very dilute sodium hydroxide solution. This method is disadvantageous, since large amounts of water have to be evaporated at the drying stage owing to the very dilute nature of the sodium hydroxide solution.

EP-A-0 303 440 describes the production of a hydrated crosslinked gel polymer which has 10 to 50 mol % of the acid-functional monomers neutralized and which is adjusted to the desired ultimate degree of neutralization by adding a neutralizing agent in a reaction vessel having a plurality of rotary shafts each fitted with stirring blades. True, this process provides homogeneous neutralization, since new surfaces are constantly being generated for the gel particles, but the shearing force on the gel is too high and leads to an undesirable increase in extractables.

EP-A-0 238 050 claims a process for the batchwise production of finely divided crosslinked water-absorbing polymers by conducting the polymerization in a kneader and having a degree of neutralization for the (meth)acrylic acid in the range from 0 to 100 mol %. The polymerization batch is neutralized to the desired ultimate pH in the kneader used for the polymerization, either during the polymerization or subsequently thereto. This again provides homogeneous neutralization, but the shearing forces applied are too high, so that an undesirable increase in the extractables content occurs.

In U.S. Pat. No. 5,453,323 and EP-A-0 530 438, acrylic acid is used together with water-soluble hydroxyl-containing polymers to prepare under adiabatic conditions and without neutralization of the monomers polymer gels which are subsequently comminuted in an unspecified meat grinder. The neutralizing agent is added to this comminuted gel and the mixture is again chopped. The postcrosslinker is then added and the gel is again chopped three times in order that all the reactants may be incorporated in the gel in a homogeneous manner. This repeated chopping of the gel exerts an undesirable shearing stress on the gel, elevating the level of extractables.

EP-A-0 629 411 describes the polymerization of acrylic acid with crosslinkers. The gel obtained is subsequently partially neutralized with an alkali metal salt and further crosslinked by addition of a crosslinker. The method of neutralization is not further specified in the reference; one example mentions kneading the gel with the neutralizing agent in an extruder.

DE-A-195 29 348 describes preparing superabsorbent polymers by polymerizing a partially preneutralized monomer solution under adiabatic conditions. The degree of preneutralization of the acid-functional monomers is in the range from 5 to 30 mol %. The acidic gel is neutralized after its comminution in simple mixing assemblies such as a rotating drum or in a Drais mixer, the aqueous solution of the bases being introduced via nozzles or spray injectors, for example. True, this avoids any mechanical damage to the polymer gel, but cannot provide homogeneous neutralization, since the gel is not destructured in the course of the mixing with the neutralizing agent. The pH inhomogeneities of the gel in turn lead to inferior drying, which is undesirable for economic reasons.

The acidic hydrogel is preferably neutralized by destructuring and mixing it together with the neutralizing agent in a mincer comprising a system ofscrew, rotating blade, restricted flow zone and breaker plate and providing a power output of from 1,000 to 6,000 Wh/m³, preferably of from 2,500 to 5,000 Wh/m³, by passing the hydrogel through a zone having an energy dissipation density of from 400 to 800 W/l of mixing volume. The process utilizes residence times of from 5 to 30 seconds. The frequency of the rotating blade is 1–5 s⁻¹, preferably 3–4 s⁻¹. To reduce the shearing forces on mixing in the restricted flow region above the breaker plate of the apparatus, the capillaries in the breaker plate are conical. The open area of the breaker plate is from 20 to 40%, preferably from 25 to 35%, and the initial hole diameter is from 4 to 16 mm, preferably from 8 to 10 mm, coupled with a conical widening at an angle of from 8° to 20°, preferably from 10° to 15°. A mincer is similar in equipment terms to an extruder, but-exerts less shearing force.

The design described provides a combination of high mixing efficiency and of benign mechanical treatment of the mixture of hydrogel and neutralizing agent. A single-stage treatment would prove to be absolutely adequate for homogeneous distribution, avoiding the repeated mincing of the gel which would in turn lead to an undesirable increase in the shearing stress on the gel.

The choice of neutralizing agent is not critical, suitable neutralizing agents being alkali metal hydroxides, ammonia, aliphatic primary and secondary amines, alkali metal carbonates and alkali metal bicarbonates. Particular preference is given to sodium hydroxide and sodium carbonate. The neutralizing agent may be added in liquid form, for example aqueous sodium hydroxide solution, in solid form, for example sodium carbonate powder, or in gaseous form, for example ammonia.

The specific design of the mincer also makes it possible to mix other reactants or materials with the polymer gel to be neutralized according to the invention. This avoids the repeated mincing of the gel which would in turn lead to an undesirable increase in the shearing stress on the gel.

For instance, the gel may be admixed with reactants capable of reacting with free acrylic acid, for example amino acids such as cysteine or lysine, hydroxylamine and/or its salts such as hydrochloride or sulfate, hydrazine and/or its salts, ozone or sulfur compounds having a reducing effect, such as alkali metal sulfites, bisulfites or disulfites, sodium thiosulfate or mercapto compounds.

The gel may also be admixed with materials capable of reacting with the carboxyl groups of the hydrogel by crosslinking. Examples of such materials are polyhydric alcohols, polyacid amines, polyamidoamines and their reaction products with epichlorohydrin, di- and polyepoxides, bis- and polyaziridines, bis- and polyoxazolines, di- and polyisocyanates, ethylene carbonate or oxazolidone.

It is further possible in this stage to mix the gel with fines of superabsorbent polymers that are obtained, for example, from the production of water-swellable hydrophilic hydrogels during the grinding and subsequent classification of the dried hydrogels.

The acidic hydrogel may also be neutralized according to a two-step process. In this process, the first step comprises setting a degree of neutralization of not less than 50% by weight, preferably not less than 55% by weight, particularly preferably not less than 60% by weight, in a mincer which meets the above-described conditions. The second step raises the degree of neutralization to the desired ultimate degree of neutralization by spraying the hydrogel particles with a neutralizing agent or its aqueous solution, i.e., without mechanical shearing of the gel particles. The neutralizing agent in the second step may be identical or different from the neutralizing agent in the first step. The second neutralization step is preferably carried out using aqueous sodium hydroxide solution.

Various ways are known for drying hydrogel particles. For instance, they may be dried by the thin film drying process, for example by means of a biaxial can dryer; by the plate drying process, whereby the hydrogel polymer particles are loaded onto plates in several layers in a drying chamber in which hot air circulates; by the rotating drum process using can dryers; or by the conveyor belt process, hereinbelow also referred to as simply belt drying. Drying is preferably carried out with can dryers or by the operations of belt drying, where foraminous trays of a circle conveyor are loaded in a tunnel with the material to be dried and the material is dried by blowing hot air through the tray holes during the passage through the tunnel.

The dried hydrogel is precomminuted where appropriate and then ground, preferably by means of a roll mill in order that the production of fines may be minimized. Sieving is carried out subsequently to set the particle size distribution, which is generally in the range from 100 to 1000 µm, preferably from 120 to 850 µm. Oversize particles may be resubmitted to grinding, while undersize particles may be recycled back into the production process, for example by mixing with the gel to be neutralized in the postneutralization step in the mincer, or be used for distinct purposes.

In a preferred embodiment of the invention, the absorption properties of the hydrophilic, highly swellable hydrogels thus obtained are still further improved by a subsequent surface postcrosslinking step. In this step, compounds capable of reacting with the carboxyl groups of the hydrogel by crosslinking are applied to the surface of the hydrogel particles, preferably in the form of an aqueous solution. Useful postcrosslinking agents include for example di- or polyglycidyl compounds such as phosphonyl diglycidyl ether or ethylene glycol diglycidyl ether, alkoxysilyl compounds, polyaziridines, polyamines or polyamidoamines and also their rection products with epichlorohydrin, polyols such as ethylene glycol, 1,2-propanediol, 1,4-butanediol, glycerol, di- and polyglycerol, pentaerythritol, sorbitol, the ethoxylates of these polyols and their esters with carboxylic acids or carbonic acid, ethylene carbonate, propylene carbonate, oxazolidone, bisoxazoline, polyoxazolines, di- and polyisocyanates. If necessary, acidic catalysts such as, for example, p-toluenesulfonic acid, phosphoric acid, boric acid or ammonium dihydrogenphosphate can be added.

Suitable mixing assemblies for spraying the hydrogel particles with crosslinker solution include for example Patterson-Kelly mixers, DRAIS turbulence mixers, Lbdige mixers, screw mixers, plate mixers, fluidized bed mixers, Schugi mixers. The spraying of the crosslinker solution may be followed by a temperature treatment step, preferably in a downstream dryer, at from 80 to 230° C., preferably 80–190° C., particularly preferably from 100 to 160° C., for from 5 minutes to 6 hours, preferably from 10 minutes to 2 hours, particularly preferably form 10 minutes to 1 hour; lysis products may be removed as well as solvent fractions.

In a particularly preferred embodiment of the invention the hydrophilicity of the hydrogel particle surface is additionally modified through formation of metal complexes. The formation of metal complexes on the outer shell of the hydrogel particles is effected by spraying with solutions of divalent or more highly valent metal salt solutions to allow-the-metal cations to react with the carboxyl groups of hydrogel to form complexes. Examples of di- or more highly valent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^{+}$, $La^{3+}$, $Ce^{4+}$, $Hf^{4+}$, and $Au^{+/3+}$, preferred metal cations being $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. Metal cations may be used alone or else as a mixture with each or one another. Of the metal cations mentioned, any metal salt possessing sufficient solubility in the solvent to be used is suitable. Metal salts with weakly complexing anions, for example, chloride, nitrate or sulfate, are particularly suitable. Useful solvents for the metal salts include water, alcohols, DMF, DMSO and mixtures thereof. Particular preference is given to water and water/alcohol mixtures, for example water/methanol or water/1,2-propanediol.

The spraying of the metal salt solution onto the hydrogel particles may take place both before and after the surface postcrosslinking of hydrogel particles. In a particularly preferred process, the spraying on of the metal salt solution takes place in the same step as the spraying on of the crosslinker solution, the two solutions being sprayed on separately in succession or simultaneously via two nozzles, or crosslinker solution and metal salt solution may be sprayed on together via a single nozzle.

If desired, the hydrogel particles may be further modified by admixture of finely divided inorganic solids, for example silica, alumina, titania and iron(II) oxide to further augment the effects of the surface aftertreatment. Particular preference is given to the admixture of hydrophilic silica or of alumina having an average primary particle size of from 4 to 50 nm and a specific surface area of 50–450 $m^2/g$. The admixture of finely divided inorganic solids preferably takes place after the surface modification through crosslinking/complexing, but may also be carried out before or during these surface modifications.

Hydrogels of the invention are notable for outstanding absorbency, high capillarity coupled with high gel strength and low levels of extractables and are therefore very useful as absorbents for water and aqueous fluids, especially body fluids, for example urine or blood, for example in hygiene articles such as, for example, infant and adult diapers, sanitary napkins, tampons and the like. But they may also be used as soil improvers in agriculture and market gardening, as moisture binders in cable sheathing and also for thickening aqueous wastes.

Description of test methods used in examples:

CRC (Centrifuge Retention Capacity)

0.2 g of hydrogel (particle size fraction 106–850 µm) is weighed into a teabag 60×85 mm in size, which is subsequently welded shut. The teabag is then placed in an excess of 0.9% by weight sodium chloride solution (at least 0.83 l of sodium chloride solution/1 g of hydrogel). After a swelling time of 30 minutes, the teabag is removed from the sodium chloride solution and centrifuged at 250 g for three minutes. The centrifuged teabag is weighed to determine the amount of liquid retained by the hydrogel.

Extractables (16 h)

1 g of hydrogel (particle size fraction 106–850 µm) is stirred into 200 ml of 0.9% by weight sodium chloride solution. The beaker is sealed and the mixture is stirred for 16 h. This is followed by filtration through a 0.22 µm filter and determination of the level of extractables by an acid-base titration of the carboxyl groups (titration with 0.1 normal NaOH to pH 10, then with 0.1 normal HCl to pH 2.7).

Vertical Absorption

The capillarity is determined with the aid of vertical absorption. The test apparatus consists of measuring cells and a liquid container. The measuring cells constitute a cylindrical Plexiglas tube 2.6 cm in internal diameter and 15 cm in length. The upper end of the tube is open, the lower end possesses a 36 µm sieve bottom. At a height of 3 cm (from the lower end of the tube) the tube possesses a supporting ring. The liquid container is a Plexiglas box 30.0 cm in length, 20.5 cm in width and 3.8 cm in height. At a distance of 1.5 cm to one transverse side an overflow wall 2 cm in height has been fitted. On the opposite side there is a connection to the liquid container, so that a constant level of liquid is ensured. The Plexiglas box has a removable lid which is provided with 6 circularly round holes each 3.2 cm in diameter. To perform the measurement, 1 g of hydrogel (vertical absorption 1 g) or 3 g of hydrogel (vertical absorption 3 g) is or are weighed into a measuring cell, and the hydrogel particles are uniformly distributed over the sieve bottom. The hydrogel particles are then covered with a close clearance Plexiglas disk and a close clearance Plexiglas cylinder with metal rod is introduced, the total weight of the Plexiglas disk and of the cylinder with rod being 100 g, so that the hydrogel particles are under a pressure of 19.6 $g/cm^2$. The liquid container is filled with 0.9% by weight sodium chloride solution. The measuring cell is then dipped into the liquid (to a depth of 1.2 cm) through a hole in the lid while the measuring cell is held by the supporting ring. Up to 6 measuring cells can be measured at any one time. The measuring cells are left in the liquid container for 60 minutes, during which the hydrogel particles swell and increase in weight by absorbing liquid against the force of gravity. Owing to the very high surface coverage due to hydrogel particles, a high gel layer permeability and a high capillarity are needed to obtain a high swell height. After 60 minutes, the measuring cell is removed from the liquid container and the height of the swollen gel is determined.

EXAMPLES

Example 1

In a makeup vessel 1, a mixture of 367.7 kg of demineralized water, 130.0 kg of acrylic acid, 1.0 kg of pentaerythritol triallyl ether, 220 g of 2,2'-azobisamidinopropane dihydrochioride and 400 g of potassium peroxodisulfate was deoxygenated and conditioned to 4° C. A further makeup vessel 2 was used to prepare a deoxygenated solution of 40 g of ascorbic acid in 20 kg of water. After the solutions had been prepared, the contents of the two makeup vessels were synchronously injected into a polymerization reactor under a pressure of 1.5 bar in countercurrent with nitrogen, the two solutions being mixed by a static mixer before entry into the reactor. The polymerization reactor is a 600 l tube 0.50 m in diameter with a conical taper at the end. The tubular reactor was then sealed and the reaction solution was left to stand without stirring. The ensuing polymerization, in the course of which the temperature rises to about 86° C., produces a solid gel. After cooling to room temperature overnight, a nitrogen pressure of 6 bar was injected at the top of the reactor. After the check valve situated at the end of the cone of the reactor was opened, the gel was dischargeable by means of a pump and comminuted by the action of the pump. The hydrogel was subsequently fed together with a 50% by weight solution of sodium hydroxide to a mincer characterized as follows:

| | |
|---|---|
| Power output: | 5 000 $Wh/m^3$ |
| Frequency of rotating blade: | 3 $s^{-1}$ |
| Energy dissipation density: | 750 W/l of mixing volume |
| Hydrogel residence time in mincer: | 25 s |

-continued

| | |
|---|---|
| Open area of breaker plate: | 30% |
| Hole initial diameter of open areas: | 8 mm (with conical widening to an angle of 15°), | the quantitative proportions of hydrogel and sodium hydroxide solution being chosen so as to provide a 74 mol % average degree of neutralization for the acrylic acid units of the hydrogel. The pH homogeneity of the singly minced hydrogel was verified by spraying with pH indicator solution. The hydrogel particles were then dried by means of a can drier, ground and classified to a particle size fraction of 106–850 μm. A Lödige plowshare mixer of 100 l capacity was charged with 35 kg of this hydrogel powder. A solution of 35 g of ethylene-glycol diglycidyl ether, 1170 g of water and 580 g of 1,2-propanediol was injected in the course of from 5 to 10 minutes. The product was raised to a temperature of 120° C. and maintained at 120° C. for 60 minutes to distill the solvent back off. This was followed by cooling, discharging of product and classifying to a particle size fraction of 120–850 μm. The product obtained is characterized by the following physical data, all measured in 0.9% by weight sodium chloride solution:

| | |
|---|---|
| CRC = | 32 g/g |
| Extractables (16 h) = | 1.5% |
| Vertical absorption (1 g), swell height = | 4.2 cm |

Example 2

An aluminized tetrafluoroethylene-ethylene copolymer film was secured to the surface of an endless belt made of stainless steel and having a width of 450 mm and an effective length of 3000 mm in such a way that the metallized surface was in contact with the belt surface. The endless belt was introduced into a nitrogen-filled chamber to maintain the oxygen concentration at not more than 1% by volume, while spray means were disposed in such a way that hot or cold water was sprayable onto the back of the endless belt. The endless belt moved at a speed of 100 mm/min and 15° C. water was sprayed onto the belt from below.

A makeup vessel 1 was charged with 5080 parts by weight of demineralized water, 669 parts by weight of sodium bicarbonate were suspended therein, and a mixture of 2294 parts by weight of acrylic acid and 8 parts by weight of methylenebisacrylamide was gradually metered in at a rate such that overfoaming of the reaction solution was avoided, the reaction solution cooling down to about 3–5° C. At 4° C., 2.2 parts by weight of 2,2'-azobisamidinopropane dihydrochloride (dissolved in 20 parts by weight of demineralized water) and 4 parts by weight of potassium peroxodisulfate (dissolved in 150 parts by weight of demineralized water) were added in succession and thoroughly stirred in. A second makeup vessel 2 was used to prepare a solution of 0.4 part by weight of ascorbic acid in 50 parts by weight of demineralized water.

The solutions from makeup vessels 1 and 2 were then applied continuously at a rate of 135 l/h to one end of the moving belt via a static mixer in a ratio of 80:1.

Under the abovementioned conditions, the time within which the monomer solution is subjected to polymerization on the moving belt is 30 minutes and the thickness of the monomer solution layer on the belt was about 5 cm.

At the other end of the endless belt, a polymer gel was obtained in the form of a strand about 5 cm in thickness 30 minutes from the start of the aqueous monomer solution feed. This polymer gel strand was detached from the belt surface and directly introduced into a cutting means of the roll type. This provided comminuted hydrogel particles which were introduced into the mincer described in Example 1 together with 0.9% by weight (based on acrylic acid) solid substance of a commercially available cationic polyamidoamine resin (KYMENE 557H® from Hercules Corp., USA), and also with a 50% by weight solution of sodium hydroxide, the quantitative proportions of hydrogel and sodium hydroxide solution being chosen so as to produce a 70 mol % average degree of neutralization for the acrylic acid units of the hydrogel. The pH homogeneity of the singly minced hydrogel was verified by spraying with pH indicator solution. The minced hydrogel was then hot air dried using an air temperature of 175° C., an air velocity of 1.5 m/s and a residence time of 20 minutes in the hot air stream. This provided a product which, after grinding and classifying to a particle size fraction of 106–850 μm, is characterized by the following physical data, all measured in 0.9% by weight sodium chloride solution:

| | |
|---|---|
| CRC = | 29 g/g |
| Extractables (16 h) = | 1.2% |
| Vertical absorption (1 g), swell height = | 3.8 cm |

Example 3

In a makeup vessel 1, a mixture of 367.7 kg of demineralized water, 130.0 kg of acrylic acid, 0.2 kg of allyl methacrylate, 0.5 kg of tetraallyloxyethane, 0.4 kg of divinyl adipate, 220 g of 2,2'-azobisaminopropane dihydrochloride and 350 g of potassium peroxodisulfate was deoxgenated and conditioned to 4° C. A further makeup vessel 2 was used to prepare a deoxygenated solution of 40 g of ascorbic acid in 20 kg of water. After the solutions had been prepared, the contents of the two makeup vessels were synchronously injected into the polymerization reactor described in Example 1 under a pressure of 1.5 bar in countercurrent with nitrogen, the two solutions being mixed by a static mixer before entry into the reactor. The reactor was then sealed and the reaction solution was left to stand without stirring. The ensuing polymerization, in the course of which the temperature rises to about 86° C., produced a solid gel. After cooling to room temperature overnight, a nitrogen pressure of 6 bar was injected at the top of the reactor. After the check valve situated at the end of the cone of the reactor was opened, the gel was dischargeable by means of a pump and gel comminuted by the action of the pump. The hydrogel was then fed together with a 50% by weight solution of sodium hydroxide to a mincer characterized as follows:

| | |
|---|---|
| Power output: | 4 000 Wh/m³ |
| Frequency of rotating blade: | 3 s⁻¹ |
| Energy dissipation density: | 6 000 W/l of mixing volume |
| Hydrogel residence time in mincer: | 20 s |
| Open area of breaker plate: | 32% |
| Hole initial diameter of open areas: | 10 mm (with conical widening to an angle of 12°), | the quantitative proportions of hydrogel and sodium hydroxide solution being chosen so as to produce a 74 mol % average degree of neutralization for the acrylic acid units of the hydrogel. The pH homogeneity of the singly minced hydrogel was verified by spraying with pH indicator solution. The hydrogel particles were then dried by means of a can drier, ground and classified to a particle size fraction of 106–850 μm. 6 kg of the hydrogel powder were introduced into a 10 l capacity Patterson & Kelly mixer. A solution of 10 g of bisoxazoline, 12 g of aluminum sulfate, 225 g of i-propanol and 225 g of water was then injected over 5 minutes with mixing and subsequently mixed in for 1 minute. The product was subsequently heat-treated at 185° C. in a drying cabinet for 30 minutes. It was characterized by the following physical data, all measured in 0.9% by weight sodium chloride solution:

| | |
|---|---|
| CRC = | 35 g/g |
| Extractables (16 h) = | 3.2% |
| Vertical absorption (1 g), swell height = | 4.0 cm |

Example 4

In a makeup vessel 1, a mixture of 367.7 kg of demineralized water, 130.0 kg of acrylic acid, 2.0 kg of polyethylene glycol 400 diallyl ether, 0.5 kg of triallyl-s-triazine-2,4,6 (1H,3H,5H)trione, 220 g of 2,2'-azobisaminopropane dihydrochloride and 300 g of potassium peroxodisulfate was deoxygenated and conditioned to 2° C. A further makeup vessel 2 was used to prepare a deoxygenated solution of 40 g of ascorbic acid in 20 kg of water. After the solutions had been prepared, the contents of the two makeup vessels were synchronously injected into the polymerization reactor described in Example 1 under a pressure of 1.5 bar in countercurrent with nitrogen, the two solutions being mixed by a static mixer before entry into the reactor. The reactor was then sealed and the reaction solution was left to stand without stirring. The ensuing polymerization, in the course of which the temperature rises to about 82° C., produces a solid gel. After cooling to room temperature overnight, a nitrogen pressure of 6 bar was injected at the top of the reactor. After the check valve situated at the end of the cone of the reactor was opened, the gel was dischargeable by means of a pump and comminuted by the action of the pump. The hydrogel was then fed to the mincer described in Example 3 together with 0.05% by weight of oxazolidone based on acrylic acid and a 50% by weight solution of sodium hydroxide, the quantitative proportions of hydrogel and sodium hydroxide solution being chosen so as to produce a 72 mol % average degree of neutralization for the acrylic acid units of the hydrogel. The pH homogeneity of the singly minced hydrogel was verified by spraying with pH indicator solution. The hydrogel particles were then hot air dried using an air temperature of 165° C., an air velocity of 2 m/s and a residence time of 20 minutes. After grinding and classification to a particle size fraction of 106–850 μm, 35 kg of this hydrogel powder were introduced into a 100 l capacity Lödige plowshare mixer. A solution of 70 g of polyglyceryl polyglycidyl ether (Denacol EX-5127 from Nagase Chemicals Ltd.), 10 g of citric acid, 1,300 g of water and 3900 g of methanol was injected in the course of from 5 to 10 minutes. The product was heated to that level and maintained at 150° C. for 40 minutes to distill the solvent back off. The batch was subsequently cooled, and the product discharged, blended with 0.05% by weight of hydrophilic silica (Aerosil 200) and classified to a particle size fraction of 120–850 μm. The product obtained was characterized by the following physical data, all measured in 0.9% by weight sodium chloride solution:

| | |
|---|---|
| CRC = | 30 g/g |
| Extractables (16 h) = | 2.0% |
| Vertical absorption (1 g), swell height = | 5.3 cm. |

Example 5

A makeup vessel 1 was charged with 5080 parts by weight of demineralized water, 500 parts by weight of sodium bicarbonate were suspended therein, and a mixture of 2412 parts by weight of acrylic acid and 20 parts by weight of allyl methacrylate was gradually metered in at a rate such that overfoaming of the reaction solution was avoided, the reaction solution cooling down to about 3–5° C. At 4° C., 2.5 parts by weight of 2,2'-azobisaminopropane dihydrochloride (dissolved in 20 parts by weight of demineralized water) and 4 parts by weight of potassium peroxodisulfate (dissolved in 150 parts by weight of demineralized water) were added in succession and thoroughly stirred in. A second makeup vessel 2 was used to prepare a solution of 0.6 part by weight of ascorbic acid in 50 parts by weight of demineralized water.

The solutions from makeup vessels 1 and 2 were then applied continuously at a rate of 135 l/h to one end of the moving belt of the reactor described in Example 2 via a static mixer in a ratio of 80:1.

Under the abovementioned conditions, the time within which the monomer solution was subjected to polymerization on the moving belt was 30 minutes and the thickness of the monomer solution layer on the belt was about 5 cm.

At the other end of the endless belt, a polymer gel was obtained in the form of a strand about 5 cm in thickness 30 minutes from the start of the aqueous monomer solution feed. This polymer gel strand was detached from the belt surface and directly introduced into a cutting means of the roll type. This provided comminuted hydrogel particles which were fed into the mincer described in Example 1 together with pulverulent sodium carbonate, the quantitative proportions of hydrogel and sodium carbonate being chosen so as to provide a 60 mol % average degree of neutralization for the acrylic acid units of the hydrogel. The hydrogel particles were then sprayed with 50% by weight aqueous sodium hydroxide solution in a continuous rotary tube mixer to obtain a 70 mol % ultimate degree of neutralization of the acrylic acid units of the hydrogel. This provided very loose, fluffy gels with distinct gel particles, which were hot air dried using an air temperature of 180° C., an air velocity of 2.5 m/s and a residence time of 10 minutes. After grinding and classification to a particle size of 106–850 μm. 35 kg of the hydrogel powder were introduced into a 100 l capacity Lödige plowshare mixer. A solution of 50 g of KYMENE 557H®, 600 g of water and 600 g of 1,2-propanediol on the one hand and a solution of 14 g of ethylene glycol diglycidyl ether, 53 g of aluminum sulfate, 840 g of water-and 360 g of 1,2-propanediol were simultaneously injected via two nozzles in the course of from 5 to 10 minutes. The product was heated to 170° C. and maintained at that level for 15 minutes to distill the solvent back off. The batch was subsequently cooled and the product discharged and classified to a particle size fraction of 120–850 μm. The product obtained was characterized by the following physical data, all measured in 0.9% by weight sodium chloride solution:

| | |
|---|---|
| CRC = | 24 g/g |
| Extractables (16 h) = | 1.8% |
| Vertical absorption (3 g), swell height = | 5.4 cm |

The hydrogels obtained according to Examples 1 to 5 are notable for outstanding absorbency coupled with high capillarity and low extractables contents, and are therefore very useful as absorbents for water and aqueous fluids, especially body fluids, for example urine or blood, for example in hygiene articles such as, for example, infant and adult diapers, sanitary napkins, tampons and the like.

We claim:

1. A hydrophilic, highly swellable hydrogel based on (co)polymerized monomers or based on graft (co)polymers and prepared by
   a) free-radically (co)polymerizing one or more hydrophilic monomers

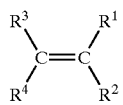

(I)

where
   $R^1$ is hydrogen, methyl or ethyl,
   $R^2$ is —COOR$^4$, hydroxysulfonyl, phosphonyl, a ($C_1$–$C_4$)-alkanol-esterified phosphonyl group or a group of the general formula (II)

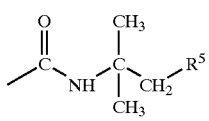

(II)

$R^3$ is hydrogen, methyl, ethyl or carboxyl,
   $R^4$ is hydrogen, amino-($C_1$–$C_4$)-alkyl or hydroxy-($C_1$–$C_4$)-alkyl, and
   $R^5$ is hydroxysulfonyl, phosphonyl or carboxyl; or graft (co)polymerizing one or more hydrophilic monomers of the formula (I) onto a grafting base, the average degree of neutralization of the acid-functional monomers being from 0 to 40 mol %;
   b) comminuting the acidic hydrogel;
   c) neutralizing the acidic hydrogel to an ultimate degree of neutralization of 50–85 mol % by adding a neutralizing agent; and
   d) drying, grinding and sieving the hydrogel particles characterized by
      a centrifuge retention of at least 29 g/g for a 0.9% aqueous NaCl solution, and
      a vertical absorption (1 g) swell height of at least 3.5 cm coupled with an extractables content (16 h value) of less than 5%; or
      a centrifuge retention of at least 23 g/g for a 0.9% aqueous NaCl solution, and
      a vertical absorption (3 g) swell height of at least 5 cm an extractables content (16 h value) of less than 4%.

2. The hydrophilic, highly swellable hydrogel of claim 1, wherein the polymerization is carried out quiescently.

3. The hydrogel of claim 1, wherein suitable grafting bases are selected from the group consisting of starch, starch derivatives, cellulose, cellulose derivatives, polyvinyl alcohol, polyalkylene oxide, polyethylene oxide, polypropylene oxide and hydrophilic polyesters.

4. The hydrogel of claim 1, wherein the (co)polymerizing of the hydrophilic monomers is effected in the presence of crosslinkers.

5. The hydrogel of claim 1, wherein the acidic hydrogel is neutralized to an ultimate degree of neutralization of 50–85 mol % by mixing with a neutralizing agent in a mincer comprising a system of screw, rotating blade, restricted flow zone and breaker plate, wherein
   a) the mincer has a power output of from 1000 to 6000 Wh/m$^3$.
   b) the hydrogel is passed through a zone having an energy dissipation intensity of from 400 to 800 W/l of mixing volume,
   c) the average hydrogel residence time in the mincer is from 5 to 30 seconds,
   d) the open area of the breaker plate is from 20 to 40% and the postneutralized hydrogel particles are subjected to the drying step without further shearing.

6. The hydrogel of claim 1, wherein, as well as the neutralizing agent, one or more other reactive materials capable of reacting with free acrylic acid and/or with the carboxyl groups of the hydrogel and/or water-swellable hydrophilic polymer fines are added during the neutralization of the gel.

7. The hydrogel of claim 1, wherein the postneutralization is carried out in two steps, the first neutralization step taking place in the mincer and the second neutralization step being effected by applying the neutralizing agent to the hydrogel particles without mechanical shearing stress.

8. The hydrogel of claim 1, wherein the dried and ground hydrogel particles are covalently surface postcrosslinked.

9. The hydrogel of claim 1, wherein the surface of the dried and ground hydrogel particles is modified by the formation of metal complexes.

10. A method of absorbing water or aqueous fluid, comprising contacting the hydrogel according to claim 1 with water or aqueous fluid.

11. A method of absorbing bodily fluid, comprising contacting the hydrogel according to claim 1 with bodily fluid.

12. An absorbent, comprising the hydrogel according to claim 1.

13. A method of absorbing water or aqueous fluid, comprising contacting the absorbent according to claim 12 with water or aqueous fluid.

14. A method of absorbing bodily fluid, comprising contacting the absorbent according to claim 12 with bodily fluid.

15. A diaper, comprising the hydrogel according to claim 1.

16. A method of absorbing water or aqueous fluid, comprising contacting the diaper according to claim 15 with water or aqueous fluid.

17. A method of absorbing bodily fluid, comprising contacting the diaper according to claim 15 with bodily fluid.

18. A tampon, comprising the hydrogel according to claim 1.

19. A method of absorbing water or aqueous fluid, comprising contacting the tampon according to claim 18 with water or aqueous fluid.

20. A method of absorbing bodily fluid, comprising contacting the tampon according to claim 18 with bodily fluid.

21. A sanitary napkin, comprising the hydrogel according to claim 1.

22. A method of absorbing water or aqueous fluid, comprising contacting the sanitary napkin according to claim 21 with water or aqueous fluid.

23. A method of absorbing bodily fluid, comprising contacting the sanitary napkin according to claim 21 with bodily fluid.

* * * * *

UNITED STATES PATENT AND TRADEMARK OFFICE
CERTIFICATE OF CORRECTION

PATENT NO. : 6,602,950 B1
DATED : August 5, 2003
INVENTOR(S) : Dentler et al.

It is certified that error appears in the above-identified patent and that said Letters Patent is hereby corrected as shown below:

<u>Title page,</u>
Item [45] and the Notice information should read as follows:
-- [45]  **Date of Patent:  \*Aug. 5, 2003**
  [\*]   Notice: Subject to any disclaimer, the term of this patent is extended or adjusted under 35 U.S.C. 154(b) by 0 days.

This patent is subject to terminal disclaimer--

Signed and Sealed this

Eleventh Day of November, 2003

JAMES E. ROGAN
*Director of the United States Patent and Trademark Office*